United States Patent
Weekamp et al.

(10) Patent No.: US 12,150,786 B2
(45) Date of Patent: Nov. 26, 2024

(54) SENSOR ARRANGEMENT FOR MOUNTING ON A GUIDEWIRE OR CATHETER

(71) Applicant: KONINKLIJKE PHILIPS N.V., Eindhoven (NL)

(72) Inventors: Johannes Wilhelmus Weekamp, Beek en Donk (NL); Antonia Cornelia Van Rens, Nuenen (NL); Roland Alexander Van De Molengraaf, Geldrop (NL); Arjen Van Der Horst, Tilburg (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 991 days.

(21) Appl. No.: 16/970,424

(22) PCT Filed: Feb. 18, 2019

(86) PCT No.: PCT/EP2019/053936
§ 371 (c)(1),
(2) Date: Aug. 17, 2020

(87) PCT Pub. No.: WO2019/166254
PCT Pub. Date: Sep. 6, 2019

(65) Prior Publication Data
US 2021/0106280 A1    Apr. 15, 2021

(30) Foreign Application Priority Data
Feb. 27, 2018   (EP) ..................................... 18158860

(51) Int. Cl.
*A61B 5/00* (2006.01)
*A61B 5/0215* (2006.01)
(Continued)

(52) U.S. Cl.
CPC ............ *A61B 5/6851* (2013.01); *G01D 11/30* (2013.01); *A61B 5/0215* (2013.01); *A61B 5/026* (2013.01);
(Continued)

(58) Field of Classification Search
CPC ... A61B 5/6851; A61B 5/02158; A61B 5/026; A61B 2562/222; A61B 2562/227; A61B 2562/04; A61B 2562/166
See application file for complete search history.

(56) References Cited

U.S. PATENT DOCUMENTS 5,113,868 A * 5/1992 Wise ................... A61B 5/02158
73/714
5,210,846 A   5/1993 Lee
(Continued)

FOREIGN PATENT DOCUMENTS

| EP | 2829227 A1 | 1/2015 |
|---|---|---|
| JP | 2014072331 A * | 4/2014 |
| WO | 2014105442 A1 | 7/2014 |

OTHER PUBLICATIONS

JP 2014072331 A English Translation (Year: 2014).*
International Search Report & Written Opinion of PCT/EP2019/053936, dated Jun. 17, 2019.

*Primary Examiner* — Daniel L Cerioni
*Assistant Examiner* — Andrew E Hoffpauir

(57) ABSTRACT

A sensor arrangement is for mounting along an elongate device. The sensor arrangement is for positioning along a line sensor arrangements and has terminal blocks at a proximal and distal side, each for connection to one or more wires. A connection circuit controls the coupling of sensor signals to the proximal wires and the coupling of the distal wires to the proximal wires. In this way, a bypass function is implemented through the connection circuit, which avoids (Continued)

the need for physical wires of a distal sensor arrangement to bypass the sensor arrangement itself.

19 Claims, 3 Drawing Sheets

(51) Int. Cl.
*A61B 5/026* (2006.01)
*A61B 5/1473* (2006.01)
*A61B 8/12* (2006.01)
*G01D 11/30* (2006.01)

(52) U.S. Cl.
CPC ........... *A61B 5/1473* (2013.01); *A61B 5/6852* (2013.01); *A61B 8/12* (2013.01); *A61B 2562/063* (2013.01)

(56) References Cited

U.S. PATENT DOCUMENTS

| | | |
|---|---|---|
| 2005/0054905 A1 | 3/2005 | Corl |
| 2005/0148832 A1* | 7/2005 | Reghabi ............... A61B 5/4839 600/561 |
| 2005/0268724 A1 | 12/2005 | Tenerz |
| 2006/0129061 A1* | 6/2006 | Kaneto ............. A61M 25/0043 600/561 |
| 2009/0160289 A1 | 6/2009 | Wilser |
| 2014/0187874 A1* | 7/2014 | Burkett ................ A61B 5/6851 600/301 |
| 2014/0257107 A1* | 9/2014 | Rice ......................... A61B 8/12 600/459 |
| 2015/0342530 A1* | 12/2015 | Dekker .................. A61B 1/051 600/478 |
| 2017/0112405 A1 | 4/2017 | Sterrett |
| 2017/0127985 A1* | 5/2017 | Thompson .......... A61B 5/14532 |
| 2017/0202495 A1 | 7/2017 | Dalene |
| 2017/0251913 A1* | 9/2017 | Birnkrant ............... H05K 1/189 |
| 2019/0217059 A1* | 7/2019 | Meyer .................. H05K 7/1427 |

* cited by examiner

SENSOR ARRANGEMENT FOR MOUNTING ON A GUIDEWIRE OR CATHETER

CROSS-REFERENCE TO PRIOR APPLICATIONS

This application is the U.S. National Phase application under 35 U.S.C. § 371 of International Application No. PCT/EP2019/053936, filed on Feb. 18, 2019, which claims the benefit of European Patent Application No. 18158860.9 filed on Feb. 27, 2018. These applications are hereby incorporated by reference herein.

FIELD OF THE INVENTION

This invention relates to devices which incorporate sensing functionality along a shaft such as a guidewire or catheter.

BACKGROUND OF THE INVENTION

Minimally invasive surgery methods require the implementation of sensors for imaging or for physiological parameter monitoring at the tip of and/or along guidewires and catheters.

However, the very limited size of these instruments poses an important challenge in integrating the required sensing functionality. Micro-electromechanical system (MEMS) sensors can be integrated with application-specific integrated circuit (ASIC) technology and enable advanced imaging and/or sensing functionality in a very small area.

The interconnect between the in-vivo sensors and the ex-vivo sensor system has to be optimized as well, basically meaning the number of system wires has to be minimized. A low wire count is important due to the limited space available to route the wires. For example a typical outer diameter of a coronary guidewire is 360 μm. A low wire count is also important as it simplifies the soldering or other bonding of the system wires to the sensor die.

Pressure sensor solutions for medical guidewires and catheters can be based on capacitive, piezo resistive and optic transducer technology. One known sensor solution is a capacitive pressure sensor for use in a medical guidewire. The pressure sensing guidewire is known as a pressure wire. The capacitive pressure sensing device is monolithically integrated with its readout circuit. The arrangement comprises a sensor control system at one (proximal) end of a shaft and a pressure sensor at the other (distal) end. A pair of electrical wires runs along the shaft. The solution uses only two electrical interface signals; one ground signal on one of the wires and one signal that carries the sensor DC supply voltage (e.g. 2.5V) and also carries a frequency modulated current as the sensor signal. This modulation is read by the sensor control system.

The connection scheme based on two signals is significant as it simplifies the soldering and bonding of the system wires to the miniaturized sensor die. The signals are transferred via two conductive ribbons from the distal end to the proximal end of the shaft, e.g. catheter.

It is also desirable to provide multiple sensors along a catheter or guidewire, so that physiological sensing can take place at different locations and/or different sensor types may be provided along a length portion of the catheter or guidewire.

The problem then arises that the electrical connection wires to a more distal sensor (i.e. one inserted further into the body) need to bypass a more proximal sensor if independent readout is desired. There is insufficient space for this physical bypass.

US 2005/0148832 A1 discloses an apparatus for sensing multiple parameters comprising a housing and a plurality of sensors disposed within the housing. The plurality of sensors are "daisy-chained" together via the interconnect. The "daisy-chaining" is facilitated by digital addressing, therefore each of the plurality of sensors includes an analog-to-digital (A/D) converter integrated circuit as well as a power supply for powering the integrated circuit. Each of the plurality of sensors may be individually addressed by a remote device, such as, for example, a computer or other controller.

There remains a need for improvement of interconnection between plurality of sensors for integration of the plurality of sensors in devices with form and spatial dimension limitations.

SUMMARY OF THE INVENTION

The invention is defined by the claims.

According to the needs of improvement of interconnection between plurality of sensors and/or integration of plurality of sensors in devices with form and spatial dimension limitations, the invention discloses the following embodiments:

a) A sensor connection arrangement for an elongate device, comprising:
   a foil configured for conduction of electrical signals, the foil comprising two terminal segments at two opposite sides of a central segment, wherein at least a portion of each of the terminal segments is bendable for allowing folding of the terminal segments of the foil over the central segment of the foil;
   two terminal structures attached and electrically connected to the respective terminal segments of the foil, wherein the terminal structures are configured to at least partially overlap with the central segment of the foil when a sensor is electrically connected to one of the terminal structures.

b) The sensor connection arrangement of a), wherein the terminal structures and the foil form a cradle, configured to receive the sensor.

c) The sensor arrangement of a) or b), further comprising two ASIC connection structures attached and electrically connected to the foil, and wherein the two terminal structures overlap with the respective ASIC connection structures when the sensor is electrically connected to one of the terminal structures.

d) A sensor arrangement comprising:
   a sensor connection arrangement of any of a) to c);
   the sensor, electrically coupled to a first of the terminal structures;
   wherein the second of the terminal structures is configured for connection to a further sensor.

e) The sensor arrangement of d), wherein the connection of the sensor to the respective terminal structure is arranged on the same side of the sensor that is configured for providing measurement signals of the surroundings.

f) The sensor arrangement of d) or e), wherein the sensor comprises one of a: a pressure sensor, an ultrasound transducer, a flow velocity sensor, a spectral sensor, a chemical sensor.

g) A sequence of sensor arrangements comprising two sensor arrangements according to any of d) to f), being said first sensor arrangement and second sensor arrangement, wherein the second terminal structure of the first sensor arrangement is electrically connected to the first terminal structure of the second sensor arrangement.

h) The sequence of sensor arrangements according to g), wherein the first and second sensors are of different type.

i) An elongate device comprising a sequence of sensor arrangements according to g) or h), wherein the first and second sensor arrangements are arranged along the length of the elongate device.

ii) The elongate device of claim i), further comprising electrical conductors electrically connected to the first terminal structure of the first sensor arrangement, for providing the measurement signals to a back-end system.

iii) The elongate device of i) or ii), further comprising an inner core, a support structure for the first and second sensor arrangements, and an outer tube comprising openings to expose the sensors of the first and second sensor arrangements to the surroundings of the elongate device.

iv) The elongate device of any of i) to iii), wherein the elongate device is a medical device.

j) The elongate device of iv), wherein the medical device is an intravascular device.

k) The elongate device of claim j), wherein the intravascular device is a guidewire with an outer diameter of less than 1 mm.

m) A system comprsing:
an elongate device of any of i) to k);
a back-end system connected to the elongate device, wherein the system is configured to identify whether measurement signals originate from the first or the second sensor.

In all embodiments where applicable, the first sensor and/or the second sensor may comprise one or more of:
a pressure transducer (e.g. capacitive, resistive, optic);
an ultrasound transducer;
a flow transducer (e.g. Doppler, thermo-electric);
spectral sensors (e.g. for tissue characterization, sensing temperature, pH, oxygen, blood gas or $CO_2$);
chemical sensors/biosensors (e.g. for sensing biomolecules or ionic strength);
physical sensors (e.g. contact sensing, voltage).

The embodiments provide a set of sensors on a device such as guidewire or catheter. As a minimum there are two sensors, but there may be many more in an in-line chain. The intermediate sensor or sensors (i.e. those other than the last one at the distal end) are of the design as described above and thus provide a pass through function to be implemented for sensor signals received from the interconnection wire or wires at the distal side. In this way, the intermediate sensors avoid the need for physical wires to bypass one sensor to reach the next. Instead, the proximal and distal wires connect to the connection circuit.

The arrangement may comprise a device which comprises an inner core, a support part for each sensor and an outer tube. The outer tube for example has a sensor opening, and the opening is partially filled with a seal to cover the wire connections.

A device as guidewire for example has a diameter less than 1 mm or a catheter has a diameter less than 5 mm.

These and other aspects of the invention will be apparent from and elucidated with reference to the embodiment(s) described hereinafter.

BRIEF DESCRIPTION OF THE DRAWINGS

Examples of the invention will now be described in detail with reference to the accompanying drawings, in which.

DETAILED DESCRIPTION OF THE EMBODIMENTS

Figure 1:
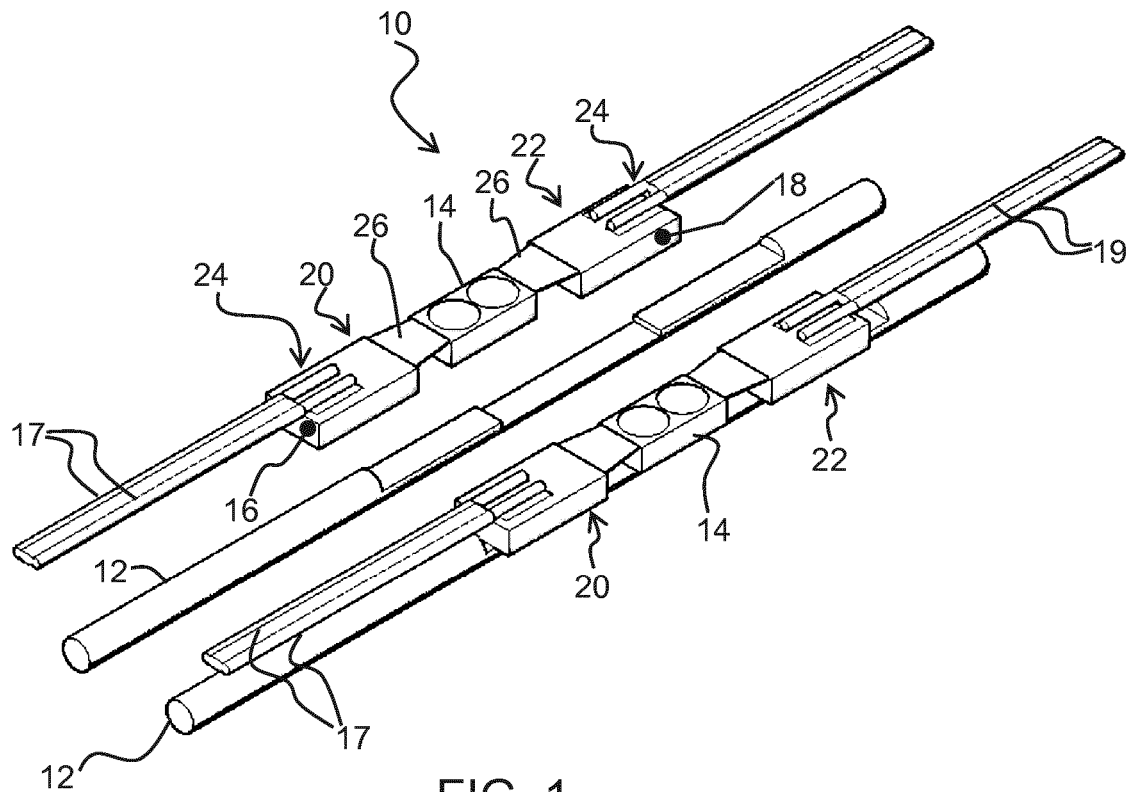
FIG. 1 shows first example of a sensor arrangement for mounting along a guidewire or catheter.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a sensor connection arrangement for mounting along a guidewire or catheter. The sensor connection arrangement together with an associated sensor defines a sensor arrangement. The sensor arrangement is for positioning along a line of sensor arrangements and has terminal blocks at a proximal side and distal side, each for connection to one or more wires, such as a pair of wires. A connection circuit controls the coupling of sensor signals to the proximal wires (and hence also to the distal wires, since they are connected to each other in the form of a bus) and the coupling of the distal wires to the proximal wires. In this way, a bypass function is implemented through the connection circuit, which avoids the need for physical wires of a distal sensor arrangement to bypass the sensor arrangement itself.

Note that "proximal" is used to indicate an end of the catheter or guidewire outside the body and "distal" is used to indicate a most inserted tip end of the catheter or guidewire.

The invention will be described below in connection with a guidewire implementation, but the same concepts may be applied to catheter sensors.

FIG. 1 shows a first example of a sensor arrangement 10 for mounting along a guidewire (or catheter). It may be considered to comprise the combination of a sensor connection arrangement and the sensor itself. It shows as separate images the sensor arrangement 10 with associated wiring connections, a separate guidewire 12, and the combination of the guidewire and the sensor arrangement.

The sensor arrangement 10 comprises a sensor 14, a first terminal block 16 at a proximal side of the sensor arrangement for connection to a pair of proximal wires 17 and a second terminal block 18 at a distal side of the sensor arrangement for connection to a pair of distal wires 19 for connecting to a further sensor arrangement at a more distal location along the guidewire 12. Thus, this example (and indeed all other examples described further below) is based on two wires connecting to the upstream and downstream sides of the sensor arrangement. However, for all examples, the same underlying concept may be applied to a single wire or to more than two wires on each side of the sensor arrangement.

A connection circuit 20, 22 is used to couple of sensor signals from the sensor 14 to the pair of proximal wires 17 and to couple the distal wires and the proximal wires so that second (and optionally further) sensor arrangement signals from the pair of distal wires 19 are combined with the local sensor arrangement signals. The part of the connection circuit which couples the proximal wires to the distal wires may simply be implemented as wire tracks. These wire tracks function as a power and a communications bus. However, the coupling of the pair of distal wires to the pair of proximal wires may be indirect, and be implemented through other circuit components such as ASICs.

The part 20 of the connection circuit which couples the (first) sensor signals to the proximal wires for example comprises a control circuit such as an ASIC which functions as a connection node for connecting to the bus. Thus, by means of the connection circuit, a shared pair of wires 17 may be provided with signals from the sensor 14 and from the sensor of a sensor arrangement further downstream along the guidewire. There is effectively a common bus to which the sensor connect locally, and the bus lines pass through the sensor connection arrangement rather than passing around the sensor connection arrangement.

The terminal blocks 16, 18 each comprise a pair of wire connection terminals 24.

The function of the ASIC 20 is to provide the sensor signal onto the lines 17 in such a way that they may be received at the back-end without interference between the sensor signals and with the origin of the sensor signals being identifiable. A serial protocol may be used for this purpose. The sensors may function as slave devices, which respond to commands provided by the master device, namely the back-end system.

One known protocol is for example the "1-Wire" (Trade Mark) serial protocol of Maxim Integrated. Each sensor then has a unique ID, and a single wire functions as the communication line as well as the power line (e.g. 2.8V to 5.25V). The other line functions as a ground line. This system allows half-duplex bidirectional communication.

An alternative approach is to use the two wires as one signal line and one power line. Other approaches may use a single wire (e.g. with local grounding at the sensor) or more than two wires.

There are various suitable communications systems, generally known as one-wire bus architectures. Thus, the encoding of sensor signals, with their respective ID, may be performed by any known mechanism. The use of sensor IDs enables multiplexing of the sensor signals as well enabling a master-slave protocol to be established. An example of a one-wire bus architecture is for example disclosed in U.S. Pat. No. 5,210,846.

There are various ways to implement the control circuit. It may for example be implemented at only one of the terminal blocks 16, 18, in which case one of the terminal blocks only functions to provide an interconnection from the associated pair of wires to the other terminal block where the control circuit is implemented.

In the example of FIG. 1, the control circuit is instead implemented at both terminal blocks. Thus, there is a proximal side connection circuit portion 20 and a distal side connection circuit portion 22. Each connection circuit portion and its associated terminal block are defined as a silicon application specific integrated circuit. The proximal side connection circuit portion may be considered to comprise the first terminal block and the distal side circuit portion 22 may be considered to comprise the second terminal block, because the terminal blocks are integrated parts of the circuit portions.

The proximal side connection circuit portion 20 performs the processing of the signals from the sensor 14 and provides these to the wires 17. It thus functions as a node controller along the bus defined by the wires 17 and 19. The distal side connection circuit portion 22 performs a function of interfacing to the wires 19.

The distal side connection circuit portion 22 is optional in that only one interface to each sensor is needed. Having circuitry on both sides may be of benefit to allow to connect more bondwires, or it may simplify the connection of wires.

In combination, the connection circuit portions thus implement a sensor interface function for the sensor 14 as well as a bypass function for sensor signals received from a more distal part of the guidewire.

The signals received from wires 19 thus comprise bus signals which may include sensor signals from a single downstream (i.e. more distal) sensor, or from a set of downstream sensors.

A conductor foil 26 is provided between the proximal side and distal side connection circuit portions 20, 22. The purpose of the conductor foil is to provide electrical interconnection tracks from the distal side connection circuit portion 22 to the proximal side connection circuit portion 22. In particular, interconnections are formed between the terminals of the block 16 and the terminals of the block 18.

These interconnections may comprises direct wire connections between pairs of terminals, or they may comprise connections which are implemented through the circuit portions. In the latter case, the circuit portions perform an interface function between the conductor foil tracks and the terminals blocks.

The sensor is for example connected to the flexible foil 26 at each side by flexible hinges. The sensor 14 may be connected on the foil 26 or it may be suspended between opposite conductor foil portions (i.e. it is mounted within the overall conductor foil).

In this way, the same sensor arrangement design may be used at multiple locations along the guidewire.

Figure 2:
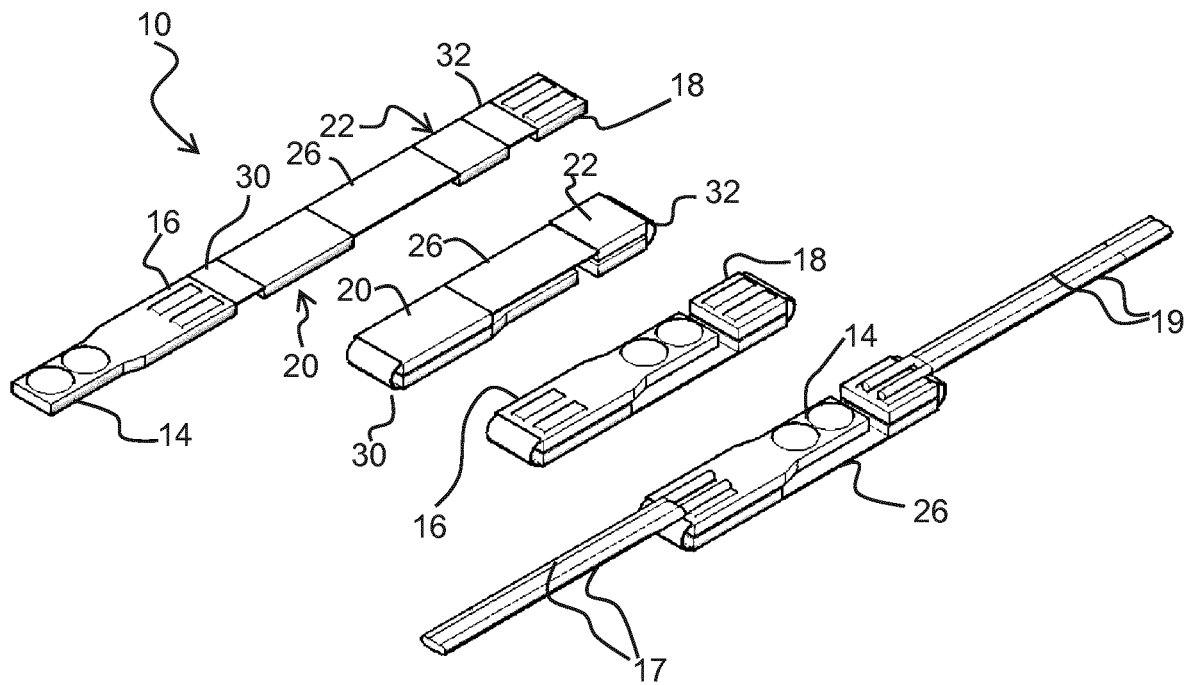
FIG. 2 shows a second example of a sensor arrangement.

FIG. 2 shows a second example of a sensor arrangement 10 again comprising a second connection arrangement and the sensor itself. This design has foldable terminal blocks. FIG. 2 shows as separate images the sensor arrangement in an unfolded state without wire connections, the sensor arrangement folded and showing one face, the sensor arrangement folded and showing an opposite face, and the folded arrangement with wire connections.

As for the example of FIG. 1, there is a proximal side connection circuit portion 20 and a distal side connection circuit portion 22 with a (first) conductor foil 26 between them. There is a second conductor foil 30 which extends in the proximal direction from the proximal side circuit portion 20 and a third conductor foil 32 extending in the distal direction from the distal side circuit portion 22. These two extra foils are foldable to enable a more compact sensor design.

The sensor arrangement is manufactured in the flat state shown and is then folded before the wires are attached.

The sensor 14 is connected to the second conductor foil 30 (at the opposite end to the circuit portion 20) and the second terminal block 18 is connected to the third conductor foil 32 (at the opposite end to the circuit portion 22). The first terminal block 16 is at the end of the sensor 14, and in the flat configuration, it is at the distal end of the sensor.

The second conductor foil 30 can be bent around to locate the sensor 14 beneath and against the first conductor foil 26. The sensor 14 comprises the first terminal block and when the second conductor foil 30 is bent over, the first terminal block 16 sits beneath and against the proximal side connection circuit portion 20. Similarly, when the conductor foil 32 is bent over, the second terminal block 18 is beneath and against the distal side connection circuit portion.

The folding of the two conductor foils 30,32 places the terminal blocks 16, 18 at the remote ends of the folded arrangement, and electrical connections to the wires 17, 19 can subsequently be made.

Figure 3:
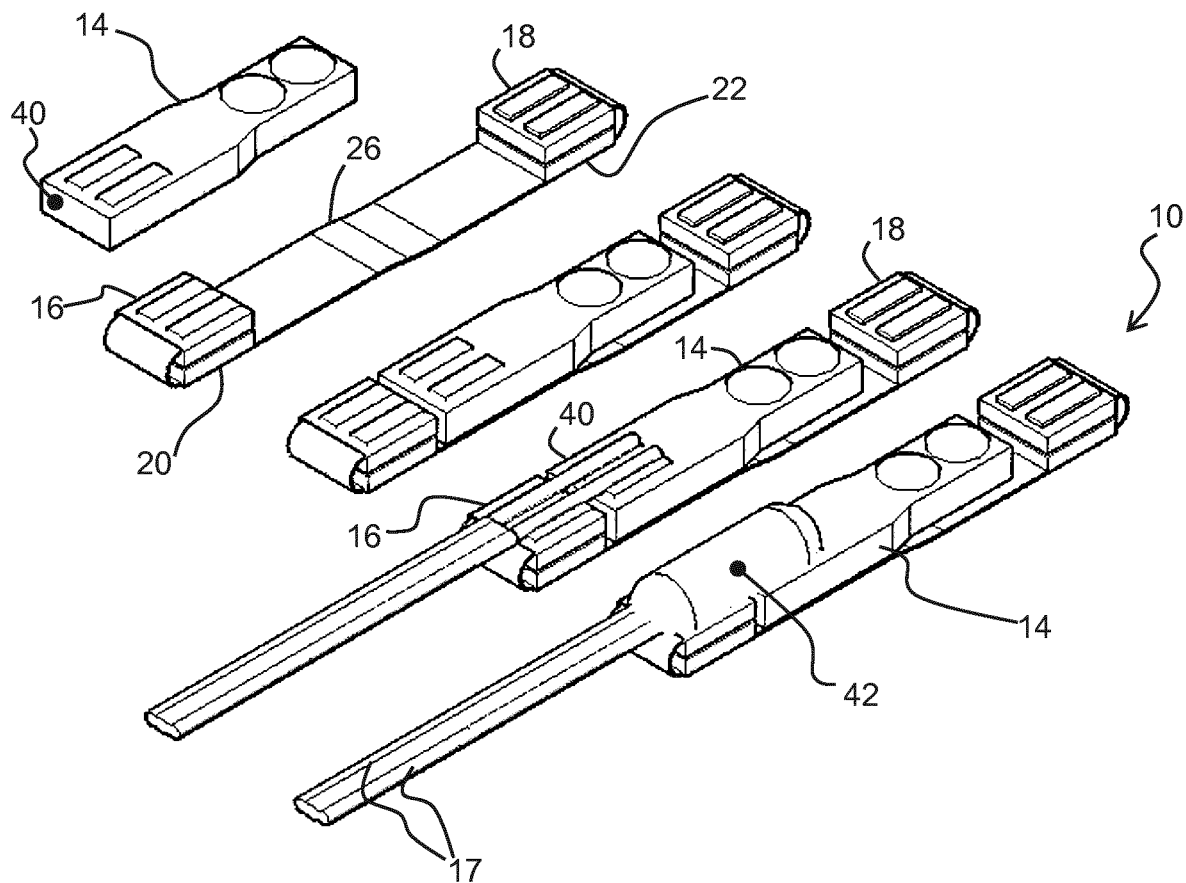
FIG. 3 shows a third example of a sensor arrangement.

FIG. 3 shows a third example of a sensor arrangement 10. This design also has foldable terminal blocks but these are separate to the sensor 14, which is then a separate modular component. Thus, there is a separate sensor connection arrangement in the form of a cradle and a sensor received by the cradle.

FIG. 3 shows as separate images the sensor 14, the cradle (i.e. the sensor connection arrangement), the sensor mounted in the cradle without wire connections, the sensor mounted in the cradle with wire connections and the sensor mounted in the cradle with sealed wire connections.

The cradle part comprises a proximal side connection circuit portion 20 and a distal side connection circuit portion 22 and a (first) conductor foil 26 between them.

As in the example of FIG. 3, there is a second conductor foil 30 extending in the proximal direction from the proximal side circuit portion 20 but in this example the first terminal block 16 (separate to the sensor) is connected to the second conductor foil 30. The second conductor foil 30 is bendable such as to locate the first terminal block 16 against the proximal side connection circuit portion 20.

As in FIG. 3, a third conductor foil 32 extends in the distal direction from the distal side circuit portion 22) and the second terminal block 18 is connected to the third conductor foil 32. The third conductor foil 32 is bendable such as to locate the second terminal block 18 against and beneath the distal side connection circuit portion 22.

The cradle is formed in a flat configuration and then folded into the shape shown.

The sensor 14 is mounted on the first conductor foil 26 between the first and second terminal blocks. The sensor has a sensor terminal block 40 so that there are three terminal blocks.

The ends of the proximal wires 17 then connect both to the first terminal block 16 and to the sensor terminal block 40, since these two terminal blocks are aligned. The terminal connections are then protected by a seal 42.

In all examples above, the sensor 14 may comprise one or more of:
a pressure transducer (e.g. capacitive, resistive, optic);
an ultrasound transducer;
a flow transducer (e.g. Doppler, thermo-electric);
spectral sensors (e.g. for tissue characterization, sensing temperature, pH, oxygen, blood gas or $CO_2$);
chemical sensors/biosensors (e.g. for sensing biomolecules or ionic strength);
physical sensors (e.g. contact sensing, voltage).

As explained above, the sensor design is for mounting at an intermediate position along a line of sensors.

Figure 4:
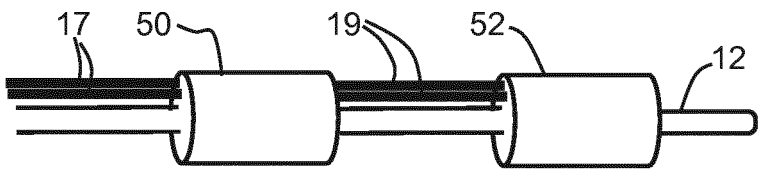
FIG. 4 shows a guidewire arrangement, comprising a guidewire, a first sensor arrangement and a second sensor arrangement mounted at different positions along the guidewire.

FIG. 4 shows a guidewire arrangement, comprising a guidewire 12, a first sensor arrangement 50 and a second sensor arrangement 52 mounted at different positions along the guidewire 12, with the second sensor arrangement 52 nearer a distal tip of the guidewire than the first sensor arrangement 50.

The pair of proximal wires 17 connect to a proximal side of the first sensor arrangement 50 and a pair of interconnecting wires 19 (i.e. which are distal wires for the sensor arrangement 50) connect between the distal side of the first sensor arrangement 50 and a proximal side of the second sensor arrangement 52.

At least the first sensor arrangement 50 is as described above. The second sensor arrangement may be of the same design. However, no connection is then needed to the distal side (second) terminal block of that sensor, since there are no more distal sensors to connect to the bus.

Figure 5:
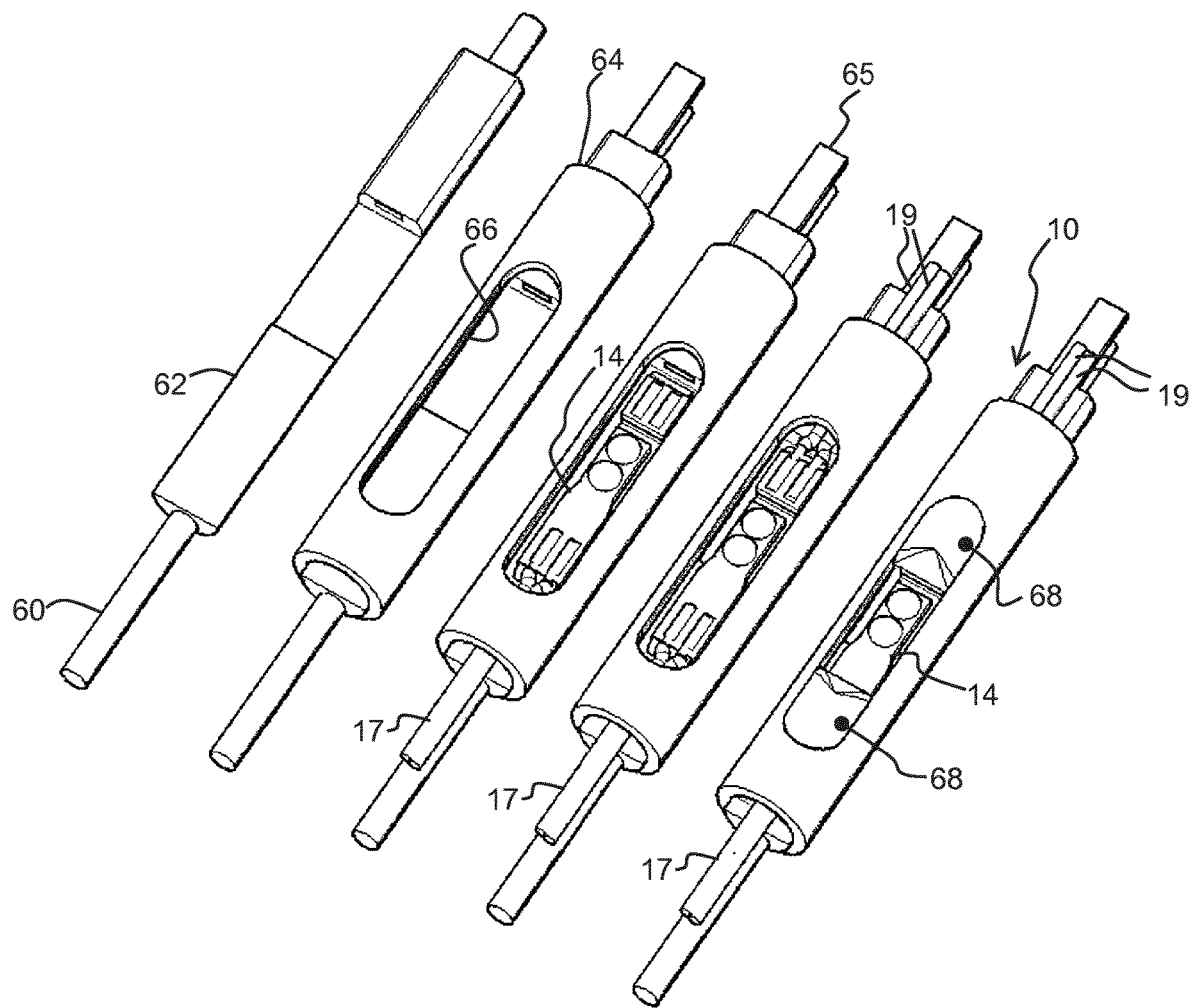
FIG. 5 shows how a sensor arrangement, such as of the type shown in FIG. 2, is integrated into a guidewire.

FIG. 5 shows how a sensor arrangement, such as of the type shown in FIG. 2, is integrated into a guidewire 12.

The guidewire comprises an inner core 60, a support part 62 for each sensor and an outer tube 64. The support part is for example made by an additive manufacturing process applied to the inner core. There is also a shaping ribbon 65 which is a metal strip which can be bent into a desired curve. This may for example be used for navigation of a guidewire through an artery.

FIG. 5 shows as separate images the inner core and support part alone, the full guidewire components of inner core, support part and outer tube, the guidewire with sensor installed and with one set of connected wires, the guidewire with sensor installed and with both sets of connected wires, and the guidewire with sensor installed with the connected wires sealed.

The outer tube 64 has a sensor opening 66. When the sensor is installed, the sensor function takes place through the opening. The wires are connected by soldering or welding through the opening and the opening is the partially filled with a seal 68 to cover the wire connections.

The invention is of interest for miniature sensors. A guidewire for example has a diameter less than 1 mm and a catheter for example has a diameter less than 5 mm. A typical example is 360 micrometers.

By way of example, the folded arrangement in FIG. 2 may have:
a length in the range 0.5 to 1.5 mm;
a width in the range 150 to 250 micrometers; and;
a thickness in the range 30 to 50 micrometers;
a pitch between the two terminals for connection to the wire pairs of 20 to 100 micrometers, such as 60 micrometers.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:
1. A sensor arrangement, comprising:
a foil configured for conduction of electrical signals;
a first terminal structure electrically coupled to the foil, wherein the first terminal structure comprises a first side and an opposite, second side, wherein the first side of the first terminal structure is attached to the foil;
a second terminal structure electrically coupled to the foil, wherein the second terminal structure comprises a first side and an opposite, second side, wherein the first side of the second terminal structure is attached to the foil; and a first sensor electrically coupled the first terminal structure, wherein the second terminal structure is configured to be electrically coupled to a second sensor, wherein the foil comprises a first fold such that the second side of the second terminal structure is positioned over the foil, wherein the foil comprises a second fold second side of the first terminal structure is positioned over the foil, wherein the first sensor is positioned over the foil between the first terminal structure and the second terminal structure.

2. The sensor arrangement of claim 1, wherein the first terminal structure, the second terminal structure, and the first sensor are positioned distal of the second fold.

3. The sensor arrangement of claim 1, wherein the first sensor and the first terminal structure comprise opposite end portions of a same component such that the first sensor and the first terminal structure are physically continuous with one another.

4. The sensor arrangement of claim 1, further comprising at least one of a first ASIC connection structure or a second ASIC connection structure, wherein the at least one of the first ASIC connection structure or the second ASIC connection structure is attached and electrically coupled to the foil, and wherein at least one of: the first terminal structure overlaps the first ASIC connection structure or the second terminal structure overlaps the second ASIC connection structure.

5. The sensor arrangement of claim 1, wherein the first sensor comprises a first side and an opposite second side, wherein the first side of the first sensor is configured for providing measurement signals of the surroundings, wherein the first sensor is electrically coupled to the first terminal structure on the first side of the first sensor.

6. The sensor arrangement of claim 1, wherein the first sensor comprises one of: a pressure sensor, an ultrasound transducer, a flow velocity sensor, a spectral sensor, or a chemical sensor.

7. A plurality of sensor arrangements, comprising:
the sensor arrangement of claim 1; and
a further sensor arrangement comprising a second sensor and a third terminal structure, wherein the second terminal structure of the sensor arrangement is electrically connected to the third terminal structure of the further sensor arrangement.

8. The plurality of sensor arrangements according to claim 7, wherein the first and second sensors are of different type.

9. An elongate device, comprising:
the plurality of sensor arrangements according to claim 7,
wherein the sensor arrangement and the further sensor arrangement are arranged along a length of the elongate device.

10. The elongate device of claim 9, further comprising electrical conductors electrically connected to the first terminal structure of the sensor arrangement and configured to provide measurement signals to a back-end system.

11. The elongate device of claim 9, further comprising an inner core, a support structure for the sensor arrangement and the further sensor arrangement, and an outer tube comprising openings to expose the first and second sensors to surroundings of the elongate device.

12. The elongate device of claim 9, wherein the elongate device is a medical device.

13. The elongate device of claim 12, wherein the medical device is an intravascular device.

14. The elongate device of claim 13, wherein the intravascular device is a guidewire with an outer diameter of less than 1 mm.

15. A system, comprising:
the elongate device of claim 9; and
a back-end system connected to the elongate device, wherein the back-end system is configured to identify whether measurement signals originate from the first sensor or the second sensor.

16. The sensor arrangement of claim 1,
wherein the first fold extends transverse to a length of the foil.

17. The sensor arrangement of claim 1, further comprising the second sensor.

18. The sensor arrangement of claim 17, wherein the first sensor and the second sensor are each a different one of: a pressure sensor, an ultrasound transducer, a flow velocity sensor, a spectral sensor, or a chemical sensor.

19. The sensor arrangement of claim 1, wherein the first terminal structure, the second terminal structure, and the sensor are positioned proximal of the first fold.

* * * * *